United States Patent
Cabelka et al.

(10) Patent No.: US 9,641,012 B2
(45) Date of Patent: May 2, 2017

(54) METHODS, IMPLANTABLE MEDICAL DEVICES, AND SYSTEMS THAT ABORT A HIGH VOLTAGE CHARGE WHEN A TRANSFORMER IS IMPAIRED

(71) Applicant: Medtronic, Inc., Minneapolis, MN (US)

(72) Inventors: Lonny Cabelka, San Clemente, CA (US); Yanina Grinberg, Plymouth, MN (US); Troy Jenison, Minneapolis, MN (US)

(73) Assignee: Medtronic, Inc., Minneapolis, MN (US)

( * ) Notice: Subject to any disclaimer, the term of this patent is extended or adjusted under 35 U.S.C. 154(b) by 152 days.

(21) Appl. No.: 14/256,864

(22) Filed: Apr. 18, 2014

(65) Prior Publication Data
US 2015/0303712 A1    Oct. 22, 2015

(51) Int. Cl.
| H02J 7/00 | (2006.01) |
| A61N 1/39 | (2006.01) |
| H02J 7/34 | (2006.01) |
| A61N 1/05 | (2006.01) |

(52) U.S. Cl.
CPC ............ *H02J 7/007* (2013.01); *A61N 1/3981* (2013.01); *H02J 7/0029* (2013.01); *H02J 7/0052* (2013.01); *A61N 1/0563* (2013.01); *H02J 7/345* (2013.01)

(58) Field of Classification Search
CPC .. A61N 1/3706; A61N 1/3718; A61N 1/3925; A61N 1/08; H02J 7/007
USPC .............................................. 607/6; 320/136
See application file for complete search history.

(56) References Cited

U.S. PATENT DOCUMENTS

| 4,233,659 A | 11/1980 | Pirkle |
| 4,394,719 A | 7/1983 | Moberg |
| 5,285,779 A | 2/1994 | Cameron et al. |
| 5,447,522 A | 9/1995 | Chang et al. |
| 5,458,621 A | 10/1995 | White et al. |
| 5,662,694 A | 9/1997 | Lidman et al. |
| 6,005,370 A | 12/1999 | Gustavson et al. |
| 6,243,604 B1 | 6/2001 | Garrett |
| 6,426,628 B1 | 7/2002 | Palm et al. |
| 6,522,920 B2 | 2/2003 | Silvian et al. |
| 6,549,807 B1 | 4/2003 | Kroll |

(Continued)

FOREIGN PATENT DOCUMENTS

WO    2012057872    5/2012

OTHER PUBLICATIONS

(PCT/US2015/025847) PCT Notification of Transmittal of the International Search Report and the Written Opinion of the International Searching Authority, Mailed Aug. 3, 2015, 9 pages.

*Primary Examiner* — Alyssa M Alter (57) ABSTRACT

High voltage charging is aborted when it is detected that a transformer providing the high voltage charge is impaired and is providing an impedance that is too low. In one instance, a voltage for a battery that provides power to the transformer is measured when the battery is substantially unloaded and a voltage is later measured when the battery is loaded during the high voltage charge. A dynamic threshold voltage is computed based on a chosen threshold impedance representing the impedance of the transformer and based the substantially unloaded voltage and on an internal resistance of the battery. When the loaded voltage is less than the threshold voltage, then the high voltage charging is aborted.

20 Claims, 5 Drawing Sheets

(56) References Cited

U.S. PATENT DOCUMENTS

| | | |
|---|---|---|
| 6,778,365 B2 | 8/2004 | Mulhauser |
| 6,799,070 B2 | 9/2004 | Wolfe et al. |
| 6,839,590 B2 | 1/2005 | Waltman |
| 6,885,894 B2 | 4/2005 | Stessman |
| 6,892,096 B2 | 5/2005 | Lyden |
| 7,235,050 B2 | 6/2007 | Schulman et al. |
| 7,509,167 B2 | 3/2009 | Stessman |
| 7,579,818 B2 | 8/2009 | Ball et al. |
| 7,619,394 B2 | 11/2009 | Pai et al. |
| 7,656,133 B2 | 2/2010 | Pai et al. |
| 8,612,167 B2 | 12/2013 | Schmidt et al. |
| 2001/0026146 A1 | 10/2001 | Wuzik et al. |
| 2005/0088145 A1 | 4/2005 | Loch |
| 2005/0143782 A1 | 6/2005 | Stessman |
| 2006/0022645 A1 | 2/2006 | Bowers |
| 2007/0150019 A1 | 6/2007 | Youker et al. |
| 2007/0179548 A1 | 8/2007 | Armstrong et al. |
| 2007/0255354 A1 | 11/2007 | Wahlstrand et al. |
| 2008/0071168 A1 | 3/2008 | Gauglitz et al. |
| 2008/0097544 A1 | 4/2008 | Gandhi et al. |
| 2009/0273318 A1 | 11/2009 | Rondoni et al. |
| 2009/0273349 A1 | 11/2009 | Rondoni et al. |
| 2010/0301803 A1 | 12/2010 | Flemming |
| 2011/0077720 A1 | 3/2011 | Torgerson et al. |
| 2011/0137359 A1 | 6/2011 | Stubbs et al. |
| 2011/0148365 A1* | 6/2011 | Doerr ................. A61N 1/08 320/162 |
| 2012/0157755 A1 | 6/2012 | D'Ambrosio |
| 2013/0197348 A1 | 8/2013 | Stancer et al. |
| 2013/0197596 A1 | 8/2013 | Cabelka et al. |

* cited by examiner

METHODS, IMPLANTABLE MEDICAL DEVICES, AND SYSTEMS THAT ABORT A HIGH VOLTAGE CHARGE WHEN A TRANSFORMER IS IMPAIRED

TECHNICAL FIELD

Embodiments relate to implantable medical devices that provide therapy that utilizes a high voltage charge. More particularly, embodiments relate to implantable medical devices that abort high voltage charges when a transformer used to create those charges becomes impaired and provides an impedance that is too low.

BACKGROUND

Implantable medical devices that provide therapy for conditions such as tachycardia and/or cardiac fibrillation must create a high voltage charge within a storage element such as a bank of capacitors. The capacitors then provide the energy for the tachycardia or defibrillation therapy. To create the high voltage charge, a battery is switched to produce pulses that are provided to a transformer that steps up the voltage.

The implantable medical device may encounter ambient conditions that can impair the transformer by saturating the transformer core. A magnetic resonance imaging (MRI) scan is one example of a situation where the ambient conditions include a large static magnetic field that may saturate the transformer core. While devices may deactivate sensing and therapy by entering a special mode designed for MRI scans, there may still be a risk that the device inadvertently exits the special mode prematurely during the MRI scan due to a device reset caused by the strong fields of the MRI machine or due to some other unforeseen reason. Alternatively, there may be a risk that the device is inadvertently not programmed into the special mode designed for MRI scans prior to the patient receiving the scan.

When the strong magnetic field of the MRI machine or other ambient condition saturates the core of the transformer, the inductance of the primary coil is drastically reduced. The primary coil then presents a very low impedance to the battery which causes the current from the battery to increase and the voltage to decrease. This spike in current may damage components of the implantable medical device including the battery.

SUMMARY

Embodiments of this disclosure address issues such as these and others by providing an implantable medical device that aborts the high voltage charge by comparing an obtained value indicative of the state of the device during the charging against a dynamic threshold. The implantable medical device obtains a value related to the battery when the battery is substantially unloaded, e.g., measuring an open circuit voltage of the battery. The dynamic threshold value may then be calculated based on a threshold impedance value for the primary coil, a value representing the resistance of the battery, and the obtained value related to the battery in the substantially unloaded state. During the high voltage charging, the value related to the battery is obtained, e.g., the loaded voltage of the battery, and is compared to the threshold value to determine whether to abort the high voltage charge due to an impaired transformer. The values related to the battery may be single measurements or may be derived from several measurements such as average values. For instance, when a threshold voltage is being used, the high voltage charge is aborted when the loaded voltage drops below the threshold voltage.

Embodiments provide a method of aborting a high voltage charge of a capacitor within an implantable medical device when a transformer of the implantable medical device that produces the high voltage charge is impaired. The method involves obtaining a substantially unloaded value for a battery of the implantable medical device that provides voltage across a primary coil of the transformer. The method further involves computing a dynamic threshold value based on the substantially unloaded value, a value representing a resistance of the battery, and a value representing a threshold impedance of the primary coil and obtaining a loaded value of the battery when performing a high voltage charge. The method also involves comparing the loaded value to the threshold value, and when the difference between the loaded value and the threshold value indicates that the transformer is impaired, then aborting the high voltage charge.

Embodiments provide a method of aborting a high voltage charge of a capacitor within an implantable medical device when a transformer of the implantable medical device that produces the high voltage charge is impaired. The method involves obtaining an open circuit voltage of a battery of the implantable medical device that provides voltage across a primary coil of the transformer and computing a dynamic threshold voltage based on the open circuit voltage, a value representing a resistance of the battery, and a value representing a threshold impedance of the primary coil. The method further involves obtaining a loaded voltage across the primary coil of the transformer when performing a high voltage charge and comparing the loaded voltage to the threshold voltage. When the loaded voltage drops below the threshold voltage then the high voltage charge is aborted.

Embodiments provide an implantable medical device that includes a battery, a transformer having a primary coil and a secondary coil, an electrical storage element connected across the secondary coil, a switch in series between the battery and the primary coil, and a voltage measurement device that is electrically connected across the battery and that is electrically connected across the primary coil when the switch is closed. The implantable medical device further includes a controller in communication with the voltage measurement device and with the switch, the controller causing the switch to open and close to begin passing current from the battery through the primary coil during a high voltage charge of the electrical storage element. Prior to the high voltage charge the controller communicates with the voltage measurement device to obtain an open circuit voltage of the battery and during the high voltage charge the controller communicates with the voltage measurement device to obtain a loaded voltage of the battery. The controller computes a dynamic threshold voltage based on the open circuit voltage, a value representing a resistance of the battery, and a value representing a threshold impedance of the primary coil. The controller compares the loaded voltage to the threshold voltage, and when the loaded voltage drops below the threshold voltage the controller then aborts the high voltage charge by leaving the switch open.

Embodiments provide an implantable medical system that includes an implantable medical lead and an implantable medical device. The implantable medical device that includes a battery, a transformer having a primary coil and a secondary coil, an electrical storage element connected across the secondary coil, a switch in series between the battery and the primary coil, and a voltage measurement device that is electrically connected across the battery and that is electrically connected across the primary coil when the switch is closed. The implantable medical device further includes a controller in communication with the voltage measurement device and with the switch, the controller causing the switch to open and close to begin passing current from the battery through the primary coil during a high voltage charge of the electrical storage element. Prior to the high voltage charge the controller communicates with the voltage measurement device to obtain an open circuit voltage of the battery and during the high voltage charge the controller communicates with the voltage measurement device to obtain a loaded voltage of the battery. The controller computes a dynamic threshold voltage based on the open circuit voltage, a value representing a resistance of the battery, and a value representing a threshold impedance of the primary coil. The controller compares the loaded voltage to the threshold voltage, and when the loaded voltage drops below the threshold voltage the controller then aborts the high voltage charge by leaving the switch open. When the high voltage charge is complete, the controller causes the energy storage element to be electrically coupled to the lead.

This summary is intended to provide an overview of the subject matter described in this disclosure. It is not intended to provide an exclusive or exhaustive explanation of the techniques as described in detail within the accompanying drawings and description below. Further details of one or more examples are set forth in the accompanying drawings and the description below. Other features, objects, and advantages will be apparent from the description and drawings, and from the statements provided below.

DETAILED DESCRIPTION

Embodiments provide implantable medical devices, systems and methods that abort high voltage charges when a primary coil of a transformer used to provide the high voltage charge becomes impaired and provides an impedance that is too low. A dynamic threshold value is computed based on battery characteristics determined while the battery is substantially unloaded, examples including the unloaded voltage level as well as internal resistance. This dynamic threshold value is then compared to a value measured during the high voltage charge to determine whether the primary coil has become impaired and is providing the impedance that is too low.

Figure 1:
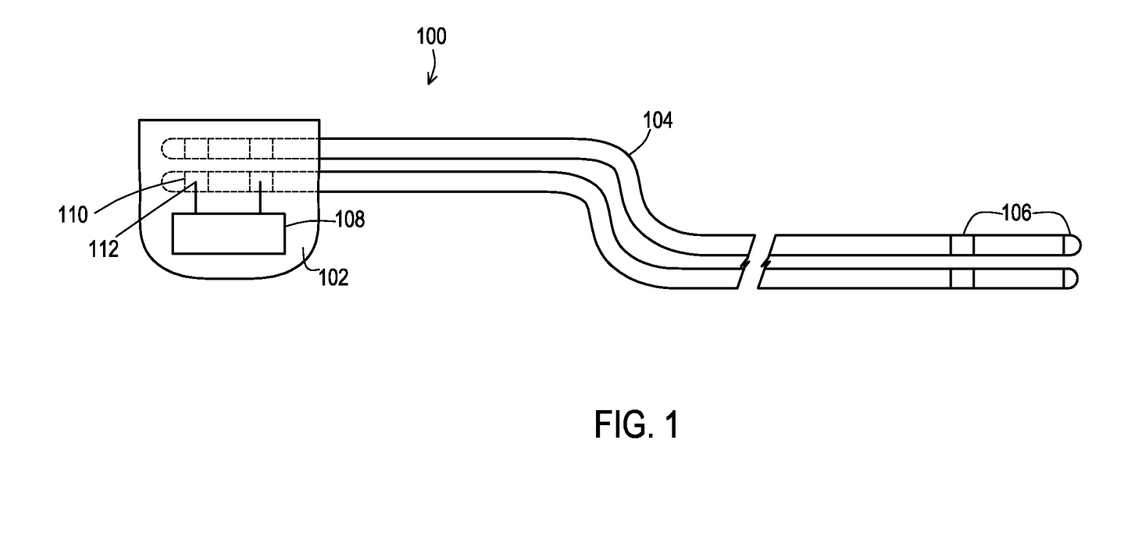
FIG. 1 shows an implantable medical system that includes an implantable medical device having one or more implantable medical leads.

FIG. 1 shows an example of an implantable medical system 100 that detects whether to abort a high voltage charge. The high voltage charge may be needed to provide a particular form of high voltage therapy, such as cardioversion and/or defibrillation. The system 100 includes an implantable medical device 102 that includes a high-voltage therapy function. The implantable medical device 102 includes circuitry 108 that provides the high-voltage therapy function including sensing for tachycardia and/or fibrillation and responding, in some instances, with a high-voltage therapy. The circuitry 108 is electrically coupled via electrical connectors 112 to proximal electrical contacts 110 of one or more leads 104 having distal electrodes 106. At least one of the leads 104 is positioned where an electrode 106 can sense the tachycardia and/or fibrillation while at least one of the leads 104 is positioned where an electrode 106 can deliver the high voltage therapy. The same lead 104 may be used to sense the tachycardia and/or fibrillation and deliver the high voltage therapy. In some instances, the system may include a single lead 104 implanted within a ventricle of the heart. In other instances, the system may include more than two leads 104. While the leads 104 are shown as examples that include two electrodes, it will be appreciated that leads with any number of electrodes may be used.

Figure 2:
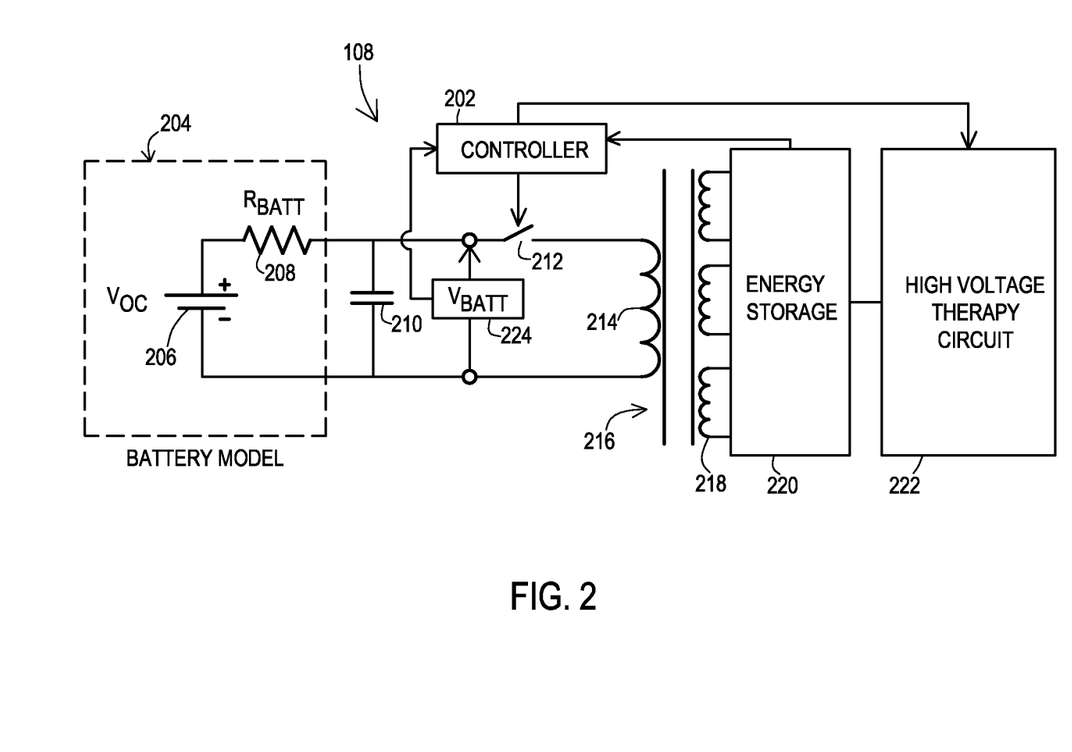
FIG. 2 shows an example of circuitry of the implantable medical device to provide a high voltage charge.

FIG. 2 shows an example of the circuitry 108 that provides the high voltage charge and the corresponding high voltage therapy. As described above, however, circuitry 108 may include other components in addition to those illustrated in FIG. 2, including transmitters, receivers, sensors, sensing circuitry, therapy circuitry and other appropriate components. The circuitry 108 includes a controller 202 that performs logical operations to control various other components. The controller 202 may be of various forms including a general purpose programmable processor, a dedicated purpose processor, hardwired digital logic, and the like. The circuitry 108 may also include a memory having computer-readable instructions that, when executed by controller 202 or other component of circuitry 108, cause controller 202 to perform various functions attributed to it in this disclosure. The memory may include any volatile, non-volatile, magnetic, optical, or electrical media, such as a random access memory (RAM), read-only memory (ROM), non-volatile RAM (NVRAM), static non-volatile RAM (SRAM), electrically-erasable programmable ROM (EEPROM), flash memory, or any other non-transitory computer-readable storage media.

The circuitry 108 also includes a battery 204 that provides a direct current (DC) voltage. The battery 204 is represented in schematic form as a voltage source 206 in series with an internal resistance 208. The voltage source 206 may be of various types including lithium ion, lithium polymer, and so forth. The voltage output by the voltage source 206 is relatively steady state but may decrease as the amount of charge within the voltage source 206 becomes depleted over time. Additionally, factors such as the degree of depletion and age may affect the amount of internal resistance 208 that is present. Each of these factors contributes to the output voltage of the battery 204 when presented with a particular impedance.

The battery 204 may be connected in parallel with a capacitor 210 to assist and stabilize the voltage being provided to the primary coil during instances of high current draw while being connected in series with a switch 212. Switch 212 may, in some instance, be implemented in silicon. The switch 212 provides a connection to the primary coil 214 of the transformer 216. The controller 202 operates the switch 212 to provide an open state and a closed state. During a high voltage charge, the controller 202 cycles the states of the switch 212 to create a train of pulses that may be transformed and also to attempt to present the battery 204 with a target impedance which may be a range of appropriate impedances. A given battery 204 may have a specified target impedance value or range of values from the manufacturer.

The transformer 216 transforms the pulses to a higher voltage that is output from the secondary coil 218 of the transformer 216. A storage element 220 that may include various individual storage elements such as individual capacitors, receives and stores the high voltage charge. The controller 202 may monitor the high voltage charge stored in storage element 220 and then upon reaching an adequate level, and possibly reconfirming the need for the high voltage therapy, release the charge via a therapy circuit that can provide a high voltage therapy of a defined pulse shape, peak, width, and so forth via the electrode 106 of the lead 104.

The controller 202 may communicate with a measurement device 224, such as an analog to digital converter, to obtain a measurement of the voltage output of the battery 204. Because the measurement device 224 is connected between the battery 204 and the switch 212, the measurement device 224 can obtain the voltage of the battery 204 regardless of whether the switch 212 is open or closed. Therefore, the measurement device 224 can provide both an open circuit measurement and a loaded measurement of the battery 204 to the controller 202. As discussed below with reference to FIGS. 3 and 4, the controller 204 can utilize both the open circuit voltage, or other substantially unloaded voltage of the battery, to compute a voltage threshold based on a current condition of the battery and then determine if the transformer 216 is impaired based on the voltage threshold compared to the loaded voltage obtained during the charge. Thus, the threshold for determining whether to abort the high voltage charge is computed dynamically to account for the present condition of the battery which reduces the likelihood of falsely aborting charges due to battery condition rather than transformer impairment.

Figure 3:
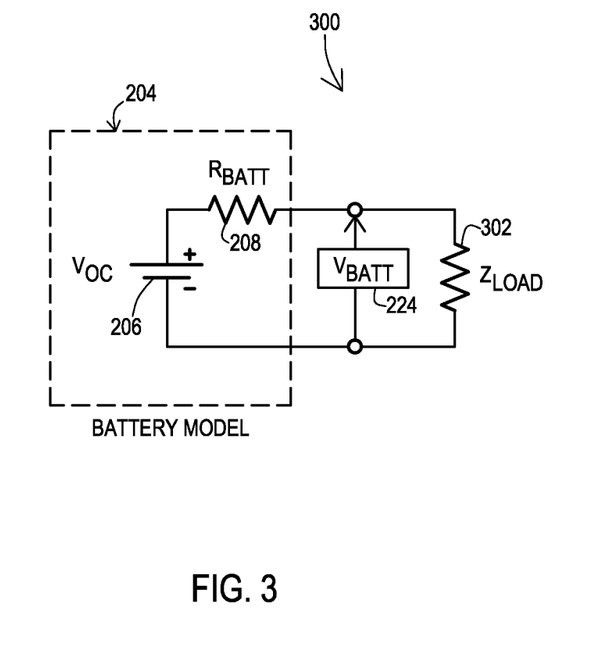
FIG. 3 shows a simplified version of the circuitry for purposes of calculating a threshold value used to abort the high voltage charge.

FIG. 3 shows a simplified circuit 300 for purposes illustrating the computation of the dynamic threshold voltage. Here, the transformer 216 and the load presented by those elements connected to the secondary coil of the transformer 216 are represented as a load impedance 302. Accordingly, the threshold voltage (Vt) can be computed as the voltage across the load impedance 302 as a function of the open circuit voltage (Voc) of the battery 204, or substantially unloaded voltage, the expected resistance of the battery (Rbatt) which is either a fixed value or may be determined by a look-up from the depletion of the battery as determined by measuring Voc, and a threshold impedance value (Zth) set for the load impedance 302 for purposes of the computation. A coefficient (C1) may be used to scale the value where C1 may equal one but may be less than one to further reduce the possibility of false aborts. This is shown as Equation 1:

$$Vt = C1 * Voc * \left[\frac{Zth}{(Rbatt + Zth)}\right]$$

The drop in impedance of the primary coil of the transformer 216 is the ultimate cause for concern, and therefore the specified threshold impedance (Zth) is ultimately the least impedance that the primary coil may present to the battery in order for the measured loaded voltage (Vbatt) during the charge to be no less than the threshold voltage (Vt). An example of a procedure for selecting the value for the threshold impedance (Zth) is discussed in more detail below with reference to FIG. 5.

This computation of the threshold voltage (Vt) utilizes the values that are known or measurable. Therefore, it is a convenient way to ultimately monitor the impedance being presented by the primary coil. Furthermore, this computation shown in Equation 1 utilizes the substantially unloaded voltage (Voc) of the battery 204 as measured such that where the measurement of Voc occurs within a relatively small amount of time from the calculation of Vt, for instance within 24 hours of measuring the loaded voltage (Vbatt), the calculation takes into account the current condition of the battery 204 which is reflected by the Voc measurement. Voc may also be computed based on multiple measurements of the substantially unloaded voltage, such as an average of measurements over the preceding week or some other recent period of time. Therefore, a condition of the battery 204 that may affect the Voc value does not falsely influence the decision to abort the high voltage charge which should be based on the impedance of the primary coil. Additionally, the Equation 1 utilizes the Rbatt value. Rbatt may be a fixed value as Voc already ensures the threshold (Vt) is based on the current condition of the battery which allows the threshold impedance (Zth) to be a chosen fixed value. However, Rbatt can be chosen to further reflect the degree of discharge of the battery 204 for batteries where Rbatt varies with the level of discharge so that the threshold voltage (Vt) is even more accurately modeled based on the present performance of the battery.

Figure 4:
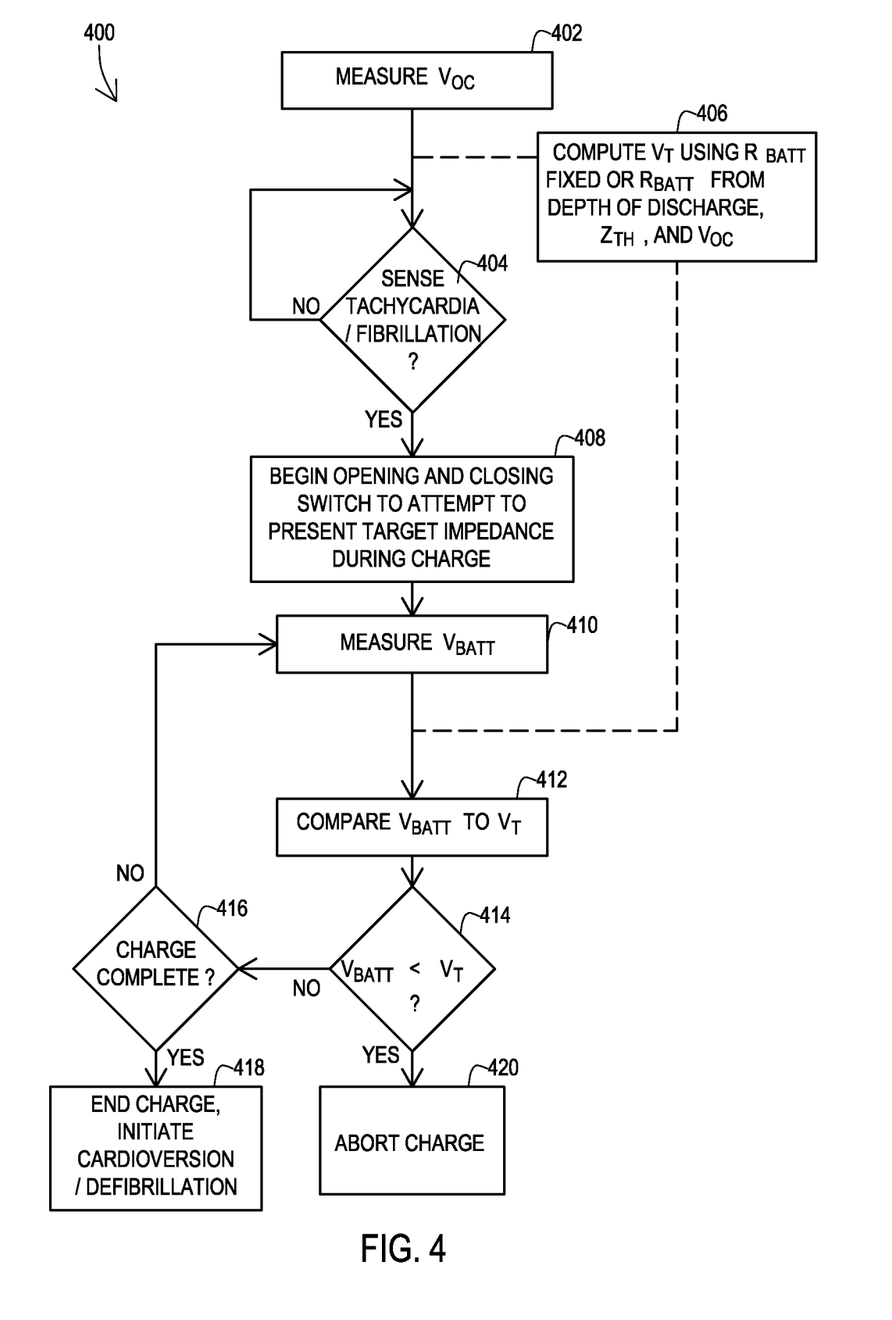
FIG. 4 shows an example of logical operations performed by the implantable medical device to determine whether to abort the high voltage charge.

FIG. 4 shows an example of a set of logical operations 400 that the controller 202 may implement to detect whether the transformer 216 has become impaired and to abort the high voltage charge when that is the case. The context for the operations 400 of FIG. 4 assumes that physiological monitoring and high voltage therapy is currently an active function for the implantable medical device 102. Thus, these operations 400 are not attempting to determine whether the monitoring and high voltage therapy is appropriate in a given circumstance. The implantable medical device 102 may perform other logical operations to determine whether a mode of operation that allows for physiological monitoring and high voltage therapy is appropriate. However, once high voltage therapy is deemed appropriate, the logical operations 400 of FIG. 4 may be implemented to avoid any consequences from continuing a high voltage charge while the transformer 216 is impaired by aborting the high voltage charge.

The logical operations 400 begin at an operation 402 where a measurement is made of the substantially unloaded voltage, such as the open circuit voltage (Voc) of the battery 204. The goal of operation 402 is to obtain the voltage of the battery 402 when there is little to no current being drawn other than the current necessary for the measurement itself such that current draw is not lowering the measured voltage. This measurement may happen at one or more set times during a day. As discussed above, this value may also be based on multiple measurements of the substantially unloaded voltage such as by taking an average of measurements made over a preceding period of time, e.g., over the preceding week.

At this point, the threshold voltage (Vt) may be calculated at an operation 406 using the available value for Rbatt, the known value for Zth, and the measured value for Voc using Equation 1. As an alternative, Vt may be calculated after other operations have occurred.

At a query operation 404, the controller 202 attempts to sense a condition such as tachycardia and/or fibrillation via an electrode 106 on a lead 104. This repeats until tachycardia and/or fibrillation is detected, and then the controller 202 begins opening and closing the switch 212 to modulate the current from the battery 204 in an attempt to present the target impedance to the battery 204, based on a normal primary coil impedance, while sending pulses to the transformer 216 at an operation 408. The duty cycle of the switch 212 may be fixed to attempt to present a fixed target impedance, for instance operating at a frequency of 55 kHz to present a 0.65 ohm load. The control of the switch 212 may also rely on monitoring of the current present in the secondary coil such that the switch 212 is returned to the closed state once current in the secondary coil has declined to approximately zero. During this charge, the controller then obtains the loaded voltage (Vbatt) from the measurement device 224 at an operation 410. This loaded voltage (Vbatt) may be a single measurement or may instead be a value based on multiple measurements, such as an average of measurements taken over a period of time. For example, the loaded voltage (Vbatt) measurements may occur at a frequency well below that of the switch, e.g., 256 Hz. If the threshold voltage (Vt) has yet to be computed, then it can be computed via the operation 406 by this point.

The controller 202 has all the information necessary to determine whether to abort the charge. At an operation 412, the controller 202 compares the value (Vbatt) measured while the battery 204 is loaded to the computed threshold value (Vt) to determine the difference between the two because this difference will indicate if the transformer is impaired and hence whether to abort the high voltage charge. At a query operation 414, when the measured value (Vbatt) is greater than or equal to the threshold value (Vt) then the transformer 216 is considered to be unimpaired so that the battery 204 is operating within an acceptable condition. In that case, the controller 202 decides whether the charge is complete at the query operation 416 by monitoring the voltage of the storage element 220. If the charge is not complete, then the controller 202 obtains another measurement or set of measurements of the battery 204 under load during the charge at the operation 410. If the charge is complete, then the controller 202 ends the charge process by leaving the switch 212 open and then, if still desired, initiating high voltage therapy such as defibrillation by the therapy circuit 222 at operation 418.

Returning to query operation 414, if it is found that the loaded value (Vbatt) is less than the threshold value (Vt), then this indicates that the transformer 216 is impaired as the battery is operating outside of an acceptable condition. The controller 202 then aborts the charge at an operation 420 by maintaining the switch 212 in the open state. While in some examples a single instance of Vbatt being less than Vt results in aborting the charge, in other examples the charge may instead be aborted once Vbatt is found to be less than Vt a certain number of times within a predefined period of time. This ensures that the Vbatt is consistently below the threshold (Vt) before aborting the charge to further avoid falsely aborting the charge. Additionally, the number of times the charge has been aborted may be tracked so that after the charge has been aborted a certain number of times, e.g., 3, which may indicate a permanent impairment of the primary coil of the transformer, the high-voltage charge may be permanently disabled.

While the determination has been discussed in relation to measuring a voltage and computing a voltage threshold, other electrical values may alternatively be used. For instance, where measurement of the electrical current is available via an electrical current measurement, the determination may be based on calculating a current value representative of the battery in a substantially unloaded state such as where a very high resistance is applied to capture the current measurement. Likewise, current may be measured during the charge process via the current measurement device. A threshold value (It) of current may be computed based on the same values of Voc, Rbatt, and Zth according to Equation 2:

$$It = Voc/(Rbatt + Zth)$$

The value specified for the threshold impedance (Zth) allows the controller 202 to discriminate between a measured loaded voltage (Vbatt) that is lower than the substantially unloaded voltage (Voc) due to a level of depletion of the battery 204 and the measured loaded voltage (Vbatt) being lower voltage due to an impaired transformer 216. Being able to discriminate between these two circumstances allows the controller 202 to avoid aborting due to the depletion level of the battery while still aborting when the transformer 216 actually is impaired.

The threshold impedance (Zth) may be set to the lowest value that is still considered to be higher than a real load impedance 302 presented by an impaired transformer 216. Such a threshold impedance (Zth) in turn results in a threshold voltage (Vt) that effectively distinguishes a low loaded voltage (Vbatt) indicative of an impaired transformer 216 from a relatively low loaded voltage (Vbatt) that is merely from a depletion level of the battery or from closely spaced repeated charge cycles which also causes a low loaded battery voltage.

Figure 5:
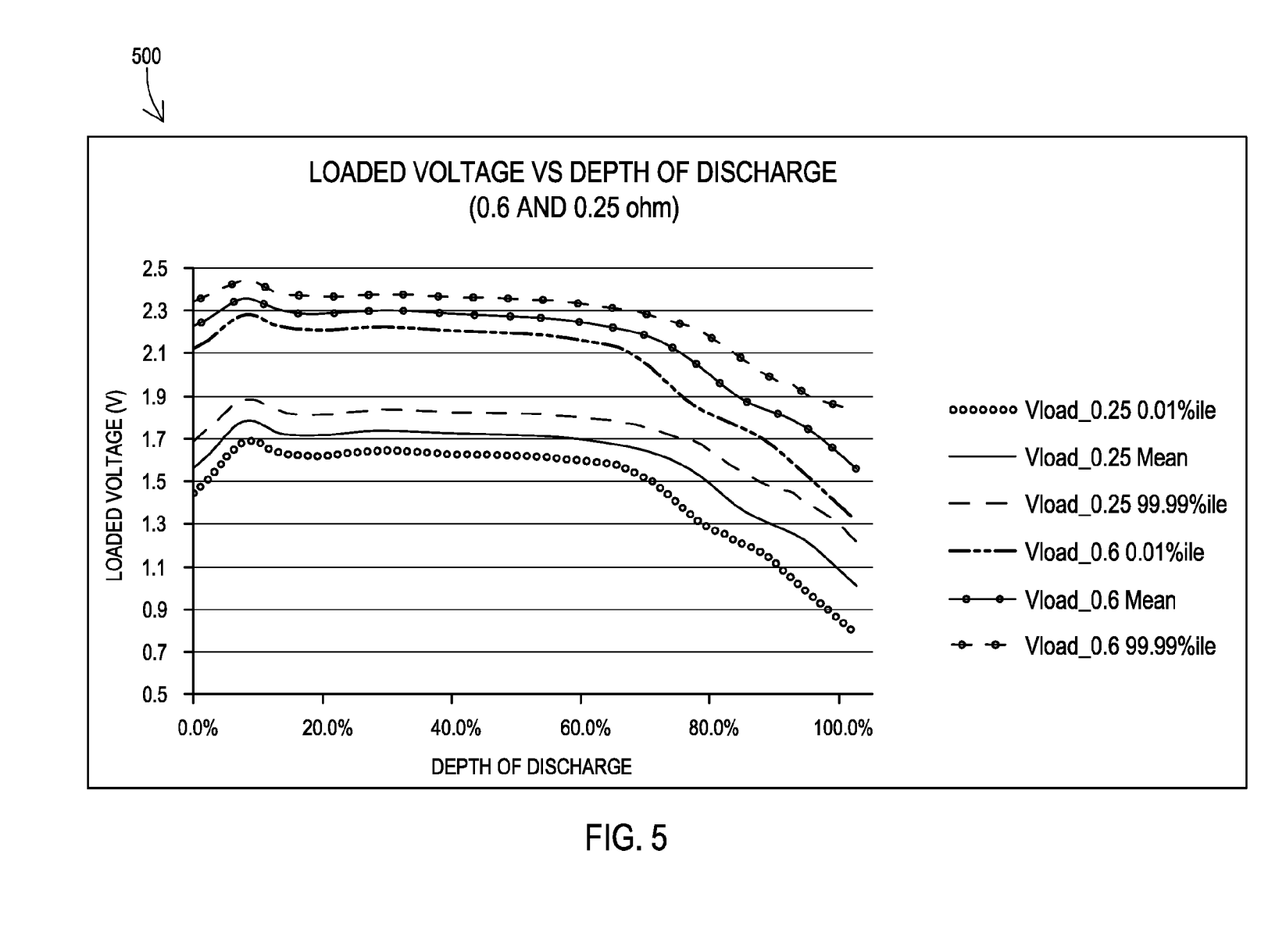
FIG. 5 shows a graph demonstration the selection of a threshold impedance for calculating the threshold value.

FIG. 5 shows a collection 500 of plots of loaded voltage over a complete range of depletion levels for a collection of batteries of a particular type where the target impedance is specified by the manufacturer as 0.6 ohms. As can be seen, when the batteries of this particular type are loaded at 0.6 ohms over the full depletion range, the least voltage being output occurs on the verge of complete depletion. The mean loaded voltage is about 1.6V while the 0.01 percentile loaded voltage is about 1.4V. As can also be seen, when the batteries of this particular type are loaded at 0.25 ohms, which is a candidate for the impedance threshold, over the full depletion range, the loaded voltage for the 99.99 percentile is less at every depth of discharge than the loaded voltage for the 0.01 percentile of the battery loaded at 0.6 ohms. Therefore, when accounting for the depth of discharge when determining the threshold voltage (Vt) by utilizing Voc, 0.25 ohm serves as an impedance threshold that will properly discriminate between a depletion level causing a relatively low voltage or an impaired transformer 216 causing the relatively low voltage.

Therefore, the value representing the threshold impedance of the primary coil may be chosen by determining a highest impedance that is less than the target impedance being presented to the battery when the transformer is unimpaired. This highest impedance being used as the threshold impedance can be found where a distribution of voltages representative of the battery 204 for any depth of discharge of the battery 204 when loaded at that highest impedance does not overlap with a distribution of voltages representative of the battery for any depth of discharge of the battery when loaded at the target impedance that is presented to the battery during the high voltage defibrillation charge when the primary coil is unimpaired.

While embodiments have been particularly shown and described, it will be understood by those skilled in the art that various other changes in the form and details may be made therein without departing from the spirit and scope of the invention.

What is claimed is:

1. A method of aborting a high voltage charge of a capacitor within an implantable medical device when a transformer of the implantable medical device that produces the high voltage charge is impaired, comprising:
   obtaining a substantially unloaded value for a battery of the implantable medical device that provides voltage across a primary coil of the transformer;
   computing a dynamic threshold value based on the substantially unloaded value, a value representing a resistance of the battery, and a value representing a threshold impedance of the primary coil;
   obtaining a loaded value of the battery when performing a high voltage charge; and
   comparing the loaded value to the threshold value, and when the difference between the loaded value and the threshold value indicates that the transformer is impaired, then aborting the high voltage charge.

2. The method of claim 1, wherein obtaining a substantially unloaded value for the battery comprises obtaining an open circuit voltage of the battery.

3. The method of claim 1, wherein computing the threshold value comprises computing a threshold voltage.

4. The method of claim 1, wherein obtaining the loaded value of the battery comprises obtaining the loaded voltage of the battery.

5. The method of claim 1, wherein comparing the loaded value to the threshold value comprises comparing a loaded voltage to a threshold voltage and when the loaded voltage drops below the threshold voltage then aborting the high voltage charge.

6. A method of aborting a high voltage charge of a capacitor within an implantable medical device when a transformer of the implantable medical device that produces the high voltage charge is impaired, comprising:
   obtaining an open circuit voltage of a battery of the implantable medical device that provides voltage across a primary coil of the transformer;
   computing a dynamic threshold voltage based on the open circuit voltage, a value representing a resistance of the battery, and a value representing a threshold impedance of the primary coil;
   obtaining a loaded voltage across the primary coil of the transformer when performing a high voltage charge; and
   comparing the loaded voltage to the threshold voltage, and when the loaded voltage drops below the threshold voltage then aborting the high voltage charge.

7. The method of claim 6, wherein obtaining the open circuit voltage of the battery occurs within 24 hours of obtaining the voltage across the primary coil of the transformer when performing a high voltage charge.

8. The method of claim 6, wherein the value representing the resistance of the battery is fixed.

9. The method of claim 6, wherein the value representing the resistance of the battery is chosen based on a depth of discharge of the battery.

10. The method of claim 6, wherein the value representing the threshold impedance of the primary coil is chosen by determining a highest impedance less than a target impedance being presented to the battery when the primary coil is unimpaired where a distribution of voltages representative of the battery for any depth of discharge of the battery when loaded at that highest impedance does not overlap with a distribution of voltages representative of the battery for any depth of discharge of the battery when loaded at the target impedance that is presented to the battery during the high voltage charge when the primary coil is unimpaired.

11. The method of claim 6, further comprising performing the high voltage charge by repeatedly opening and closing a switch in series between the battery and the primary coil of the transformer where the timing of the repeated opening and closing of the switch modulates the current through the primary coil to attempt to present the battery with a target impedance that is most accurately achieved when the transformer is unimpaired.

12. The method of claim 6, wherein obtaining the open circuit voltage comprises making a direct measurement of the open circuit voltage and wherein obtaining the loaded voltage comprises making a direct measurement of the loaded voltage.

13. An implantable medical device, comprising:
   a battery;
   a transformer having a primary coil and a secondary coil;
   an electrical storage element connected across the secondary coil of the transformer;
   a switch in series between the battery and the primary coil of the transformer;
   a voltage measurement device that is electrically connected across the battery and that is electrically connected across the primary coil when the switch is closed; and
   a controller in communication with the voltage measurement device and with the switch, the controller causing the switch to open and close to begin passing current from the battery through the primary coil during a high voltage charge of the electrical storage element, wherein prior to the high voltage charge the controller communicates with the voltage measurement device to obtain an open circuit voltage of the battery and during the high voltage charge the controller communicates with the voltage measurement device to obtain a loaded voltage of the battery, wherein the controller computes a threshold voltage based on the open circuit voltage, a value representing a resistance of the battery, and a value representing a threshold impedance of the primary coil, and wherein the controller compares the loaded voltage to the threshold voltage, and when the loaded voltage drops below the threshold voltage then aborts the high voltage charge by leaving the switch open.

14. The implantable medical device of claim 13, wherein the controller obtains the open circuit voltage of the battery within 24 hours of obtaining the voltage across the primary coil of the transformer when performing a high voltage charge.

15. The implantable medical device of claim 13, wherein the value representing the resistance of the battery is fixed.

16. The implantable medical device of claim 13, wherein the controller chooses the value representing the resistance of the battery based on a depth of discharge of the battery.

17. The implantable medical device of claim 13, wherein the value representing the threshold impedance of the primary coil is chosen by determining a highest impedance less than a target impedance being presented to the battery when the primary coil is unimpaired where a distribution of voltages representative of the battery for any depth of discharge of the battery when loaded at that highest impedance does not overlap with a distribution of voltages representative of the battery for any depth of discharge of the battery when loaded at the target impedance that is presented to the battery during the high voltage charge when the primary coil is unimpaired.

18. The implantable medical device of claim 13, wherein the controller performs the high voltage charge by repeatedly opening and closing the switch where the timing of the repeated opening and closing of the switch modulates the current through the primary coil to attempt to present the battery with a target impedance that is most accurately achieved when the transformer is unimpaired.

19. The implantable medical device of claim 13, wherein the controller obtains the open circuit voltage by the measurement device making a direct measurement of the open circuit voltage and wherein the controller obtains the loaded voltage by the measurement device making a direct measurement of the loaded voltage.

20. An implantable medical system, comprising:
   an implantable medical lead; and
   an implantable medical device, comprising:
      a battery;
      a transformer having a primary coil and a secondary coil;
      an electrical storage element connected across the secondary coil of the transformer;
      a switch in series between the battery and the primary coil of the transformer;
      a voltage measurement device that is electrically connected across the battery and that is electrically connected across the primary coil when the switch is closed; and
      a controller in communication with the voltage measurement device and with the switch, the controller causing the switch to open and close to begin passing current from the battery through the primary coil during a high voltage charge of the electrical storage element, wherein prior to the high voltage charge the controller communicates with the voltage measurement device to obtain an open circuit voltage of the battery and during the high voltage charge the controller communicates with the voltage measurement device to obtain a loaded voltage of the battery, wherein the controller computes a threshold voltage based on the open circuit voltage, a value representing a resistance of the battery, and a value representing a threshold impedance of the primary coil, wherein the controller compares the loaded voltage to the threshold voltage, and when the loaded voltage drops below the threshold voltage then aborts the high voltage charge by leaving the switch open and wherein when the high voltage charge is complete, the controller causes the energy storage element to be coupled to the lead.

* * * * *